United States Patent
Hale

(10) Patent No.: US 11,491,046 B2
(45) Date of Patent: Nov. 8, 2022

(54) COMPACT MALE CONDOM

(71) Applicant: Joshua Hale, Little Rock, AR (US)

(72) Inventor: Joshua Hale, Little Rock, AR (US)

( * ) Notice: Subject to any disclaimer, the term of this patent is extended or adjusted under 35 U.S.C. 154(b) by 0 days.

(21) Appl. No.: 16/832,132

(22) Filed: Mar. 27, 2020

(65) Prior Publication Data

US 2021/0298941 A1 Sep. 30, 2021

(51) Int. Cl.
*A61F 6/04* (2006.01)

(52) U.S. Cl.
CPC .......... *A61F 6/04* (2013.01); *A61F 2006/047* (2013.01)

(58) Field of Classification Search
CPC ...... A61F 2006/047; A61F 6/04; A61F 6/065; A61F 2006/042; Y10S 128/918; A61H 19/32

See application file for complete search history.

(56) References Cited

U.S. PATENT DOCUMENTS

| | | | |
|---|---|---|---|
| 199,444 A | 1/1878 | Wheeler | |
| 5,361,779 A * | 11/1994 | Wilson, III | A61F 6/04 128/842 |
| 5,425,379 A * | 6/1995 | Broad, Jr. | A61F 6/04 128/842 |
| 5,579,784 A * | 12/1996 | Harari | A61F 6/00 128/844 |
| 5,715,839 A | 2/1998 | Strauss et al. | |
| 6,298,853 B1 | 10/2001 | Blake | |
| 9,622,902 B1 | 4/2017 | Bublick et al. | |
| 2009/0277458 A1 | 11/2009 | McCarthy | |
| 2016/0008163 A1* | 1/2016 | Frazier | A61F 6/04 128/844 |

* cited by examiner

*Primary Examiner* — Ophelia A Hawthorne
(74) *Attorney, Agent, or Firm* — Boudwin Intellectual Property; Daniel Boudwin

(57) ABSTRACT

A compact male condom is provided having a flexible cylindrical body having a closed first end opposite an open second end defining an interior volume. The interior volume is dimensioned to receive a glans of a penis therein. A plurality of elastic rings is disposed about a circumference of the cylindrical body, wherein the plurality of elastic rings is selectively movable between an expanded position and a retracted position. The plurality of elastic rings is biased towards the retracted position.

16 Claims, 3 Drawing Sheets

COMPACT MALE CONDOM

BACKGROUND OF THE INVENTION

The present invention relates to male condoms. More particularly, the present invention pertains to a compact male condom dimensioned to secure about a glans of a penis leaving most of a shaft of the penis exposed.

Many individuals use prophylactic measures to prevent the spread of disease or minimize the risk of pregnancy as a result of sexual intercourse. Likely, the most common form of prophylactic is a male condom. Typically, these condoms secure over the entire length of the penis and secure about the base of the penis via an elastic rim. While in use, these condoms prevent any comingling of fluids, thereby reducing the risk of transmission of various sexually transmitted diseases, as well as reducing the likelihood of pregnancy. However, such condoms often suffer from an undesirable side effect of reducing sensation during intercourse as the condom covers an entirety of the penis, such that much of the sensation within the shaft of the penis is significantly reduced. Some condoms attempt to alleviate this problem by reducing the thickness of material in the condom, however this also results in more frequent breakages. Therefore, a condom that can maximize sensation for the wearer while not increasing the risk of pregnancy or sexually transmitted diseases is desired.

In light of the devices disclosed in the known art, it is submitted that the present invention substantially diverges in design elements from the known art and consequently it is clear that there is a need in the art for an improvement to existing male condoms. In this regard, the instant invention substantially fulfills these needs.

SUMMARY OF THE INVENTION

In view of the foregoing disadvantages inherent in the known types of male condoms now present in the known art, the present invention provides a male condom wherein the same can be utilized for providing convenience for the user when maximizing sensation during intercourse.

The present system comprises a flexible cylindrical body having a closed first end opposite an open second end defining an interior volume. The interior volume is dimensioned to receive a glans of the penis therein. A plurality of elastic rings are disposed about a circumference of the cylindrical body, wherein the plurality of elastic rings is selectively movable between an expanded position and a retracted position. The plurality of elastic rings are biased towards the retracted position, such that the cylindrical body is secured about the penis of the user. In some embodiments, the cylindrical body decreases in diameter from the closed first end towards the open second end, such that the cylindrical body contours to the glans.

In some embodiments, the plurality of elastic rings are disposed at regular intervals along a length of the cylindrical body, such that the force generated by the elastic rings is distributed over a larger surface area to minimize discomfort caused by wearing the compact male condom. In another embodiment, the plurality of elastic rings are spaced apart from each other in three millimeter increments. In other embodiments each elastic ring of the plurality of elastic rings comprise a circular planar member, such that an interior surface of each elastic ring rests flush against a shaft of the user's penis when the elastic rings are in the retracted position. In yet another embodiment, the plurality of elastic rings are configured to close the open second end when the plurality of elastic rings are in the retracted position.

In some embodiments, the open second end is wrapped about an applicator ring, wherein the applicator ring is configured to maintain the plurality of elastic rings in the expanded position. In another embodiment, the applicator ring comprises a rigid member, while in an alternate embodiment, the applicator ring comprises a flexible elastic member, such that the applicator ring can be removably secured over a variety of penis sizes. In yet another embodiment, the applicator ring comprises a toroidal shape, such that a smooth exterior increases comfort while the compact male condom is applied to the user's penis.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
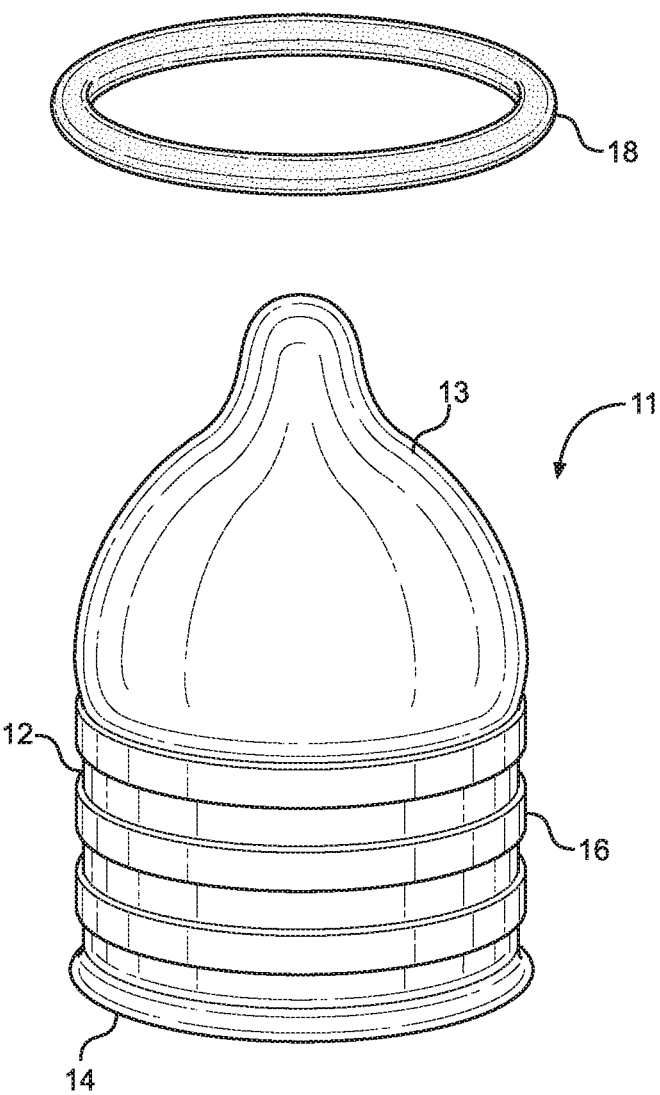
FIG. 1 shows a side view of an embodiment of the compact male condom with an applicator ring.

Reference is made herein to the attached drawings. Like reference numerals are used throughout the drawings to depict like or similar elements of the compact male condom. The figures are intended for representative purposes only and should not be considered to be limiting in any respect.

Referring now to FIG. 1, there is shown a side view of an embodiment of the compact male condom with an applicator ring. The compact male condom 11 comprises a flexible cylindrical body 12 having a closed first end 13 opposite an open second end 14 defining an interior volume. The interior volume is dimensioned to receive a glans of a user's penis therein such that the flexible cylindrical body 12 extends therearound while extending minimally over a shaft of the penis. In the illustrated embodiment, the flexible cylindrical body 12 comprises a tapered shape wherein the closed first end 13 comprises a lesser diameter than the open second end 14, thereby allowing the flexible cylindrical body 12 to contour to the user's penis. Additionally, in the illustrated embodiment the closed first end 13 further comprises a tip thereon, wherein the tip is configured to receive and store fluid excreted from the penis during use, thereby reducing the risk of breakage of the flexible cylindrical body 12. In some embodiments, the flexible cylindrical body 12 comprises a latex material, however alternate materials having similar properties commensurate with durability, impermeability, and flexibility are also contemplated to provide alternate options in the case of latex allergy.

A plurality of elastic rings 16 are disposed about a circumference of the flexible cylindrical body 12 adjacent to the open second end 14, wherein the plurality of elastic rings 16 are configured to retain the flexible cylindrical body 12 on the user's penis. In the illustrated embodiment, three elastic rings 16 are shown, however alternate configurations having greater or fewer elastic rings 16 are contemplated. Additional elastic rings 16 securing the flexible cylindrical body 12 to the user's penis provides the benefit of distributing the force adhering the flexible cylindrical body 12 to the penis across a larger surface area, thereby increasing comfort for the user. In the shown embodiment, the plurality of elastic rings 16 are disposed along the flexibly cylindrical body 12 such that the plurality of elastic rings 16 are regularly spaced, thereby ensuring even distribution of force therealong. In some embodiments, the plurality of elastic rings 16 are regularly spaced at three-millimeter increments. In the illustrated embodiment, the plurality of elastic rings 16 comprise planar members, such that an interior surface of each elastic ring of the plurality of elastic rings 16 rests flush against an exterior surface of the user's penis. The planar nature of the point of contact further distributes force across the penis, such that a user's comfort is further maintained.

The plurality of elastic rings 16 are selectively movable between an expanded position and a retracted position, wherein a diameter of the flexible cylindrical body 12 is greater when in the expanded position than in the retracted position. In this manner, the flexible cylindrical body is configured to expand to allow users of various penis sizes to utilize the compact male condom 11. In some embodiments, the plurality of elastic rings 16 are biased towards the retracted position, wherein the retracted position comprises a diameter less than that of an average penis width, thereby ensuring that the compact male condom 11 snuggly adheres to the user's penis during use. Additionally, the biased nature of the plurality of elastic rings 16 further minimizes the risk of fluid leakage from the interior volume of the compact male condom 11 when removed from the penis. In some embodiments, the retracted position of the plurality of elastic rings 16 is configured to close the open second end 14, such that a watertight seal is formed, thereby ensuring that fluids accumulated within the interior volume cannot leak therefrom.

In the illustrated embodiment, the compact male condom 11 further comprises an applicator ring 18 dimensioned to have a diameter greater than a width of the average penis, such that the applicator ring 18 can be easily placed therearound. The applicator ring 18 provides the user convenience when placing the compact male condom 11 over their penis, such that the compact male condom 11 unrolls smoothly and easily when downward force is applied to the applicator ring 18. In the illustrated embodiment, the applicator ring 18 comprises a toroidal shape, ensuring that no sharp edges are defined thereby, such that any discomfort for the user is avoided. In some embodiments, the applicator ring 18 comprises a rigid material, however, in alternate embodiments, the applicator ring 18 comprises a flexible elastic material such that the applicator ring 18 can expand to accommodate various penis sizes.

Figure 2:
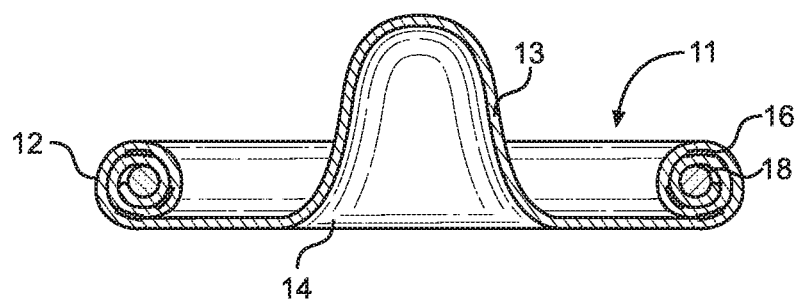
FIG. 2 shows a crass-sectional view of an embodiment of the compact male condom wrapped about the applicator ring in a storage configuration.

Referring now to FIG. 2, there is shown a cross-sectional view of an embodiment of the compact male condom wrapped about the applicator ring in a storage configuration. In the illustrated embodiment, the applicator ring 18 is wrapped within the flexible cylindrical body 12 of the compact male condom 11. In this manner, the user can apply downward pressure on the applicator ring 18 to unwrap the compact male condom 11 over the user's penis. In such an embodiment, this configuration ensures a minimal form factor, thereby providing a user with maximal convenience for portability and storage. In the shown embodiment, the closed first end 13 is centrally disposed within the applicator ring 18 when the flexible cylindrical body 12 is wrapped therearound, allowing a user to properly position the compact male condom 11, particularly to ensure the tip is properly disposed over the penis. When wrapped about the applicator ring 18, the plurality of elastic rings 16 are maintained in the expanded position, such that the user can easily apply the compact male condom 11 without struggling to widen the open second end 14. In embodiments with a rigid applicator ring 18, the applicator ring 18 ensures that the plurality of elastic rings 16 are maintained at specific width for efficient application, whereas an elastic applicator ring 18 allows the applicator ring 18 to more thoroughly conform to the user's penis. In this manner, as elastic rings 16 are removed from about the applicator ring 18 to adhere to the penis, the distance the elastic rings 16 travel between the applicator ring 18 and the retracted position over the penis is minimized, thereby preventing discomfort caused due to rapid retraction thereof.

Figure 3:
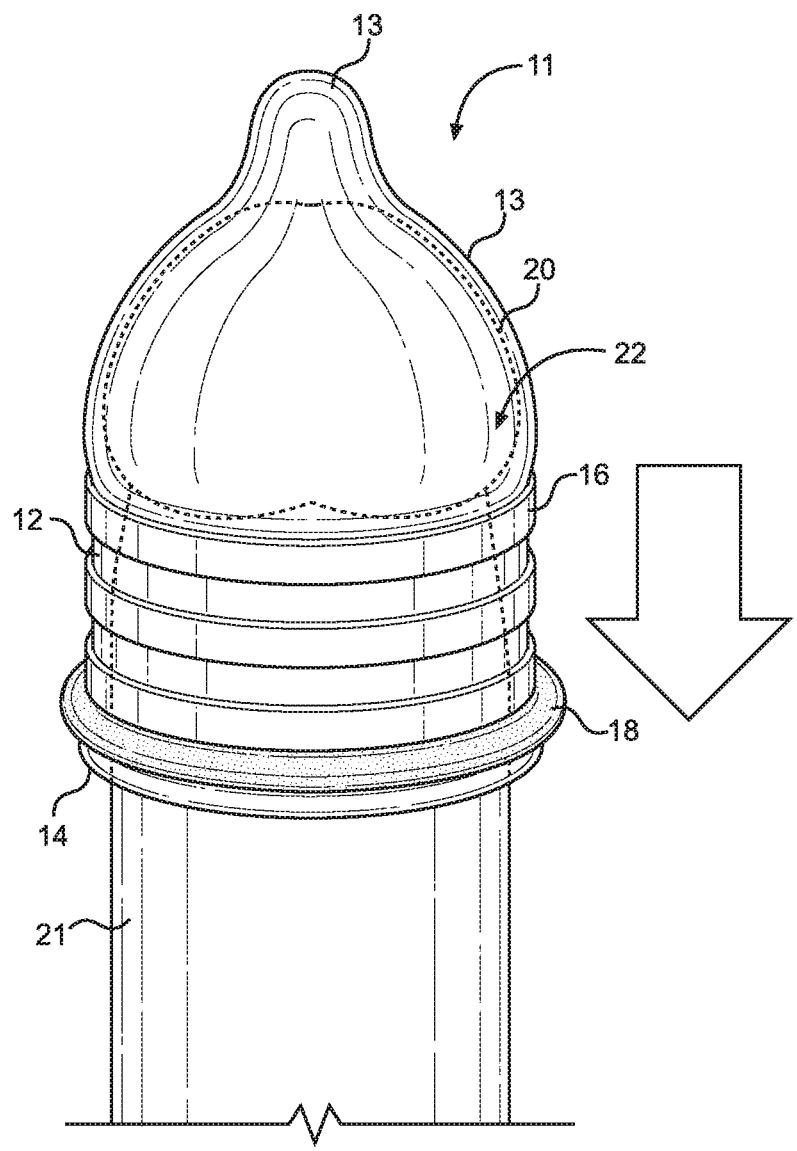
FIG. 3 shows a perspective view of an embodiment of the compact male condom being applied to a penis.
Figure 4:
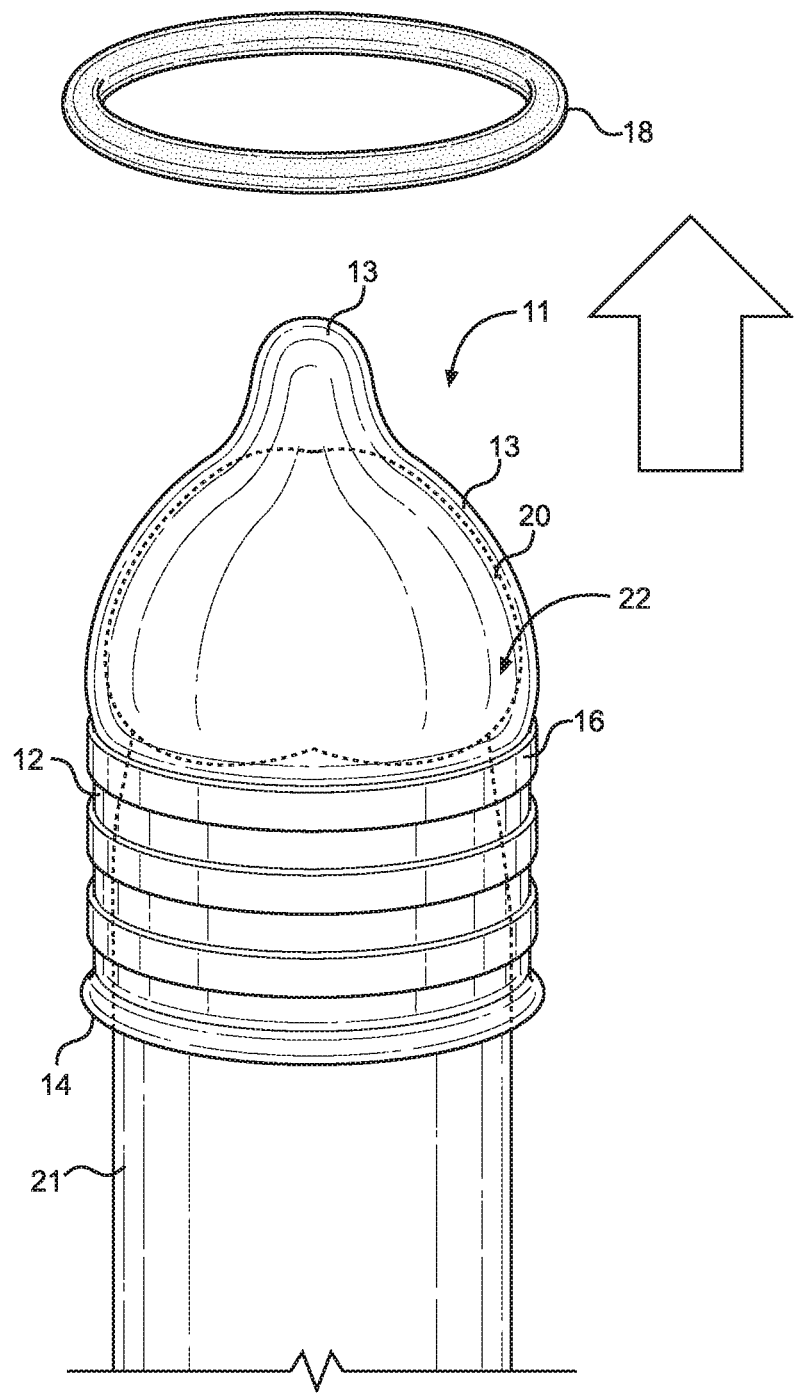
FIG. 4 shows a perspective view of the applicator ring of an embodiment of the compact male condom being removed.

Referring now to FIGS. 3 and 4, there is shown a perspective view of an embodiment of the compact male condom being applied to a penis and a perspective view of the applicator ring of an embodiment of the compact male condom being removed, respectively. In one use, the compact male condom 11 is placed over a penis 22 of the user, such that the closed first end 13 is aligned over the penis 22. The user then inserts the penis 22 through the open second end 14 such that the applicator ring 18 is placed about the penis 22 and lowered thereover such that the flexible cylindrical body 12 encapsulates a glans 20 of the penis 22. In the shown embodiment, the plurality of elastic rings 16 are disposed along the flexible cylindrical body 12 such that the elastic rings 16 are disposed only along a shaft 21 of the penis 22. As the applicator ring 18 is lowered, the plurality of elastic rings 16 disengage therefrom, thereby retracting to adhere the flexible cylindrical body 12 to the shaft 21 of the penis 22. Once the flexibly cylindrical body 12 is fully unwrapped from the applicator ring 18, the user can then remove the applicator ring 18 from the penis 22, as shown in FIG. 4. After use, the user can remove the compact male condom 11 from the penis 22, and in some embodiments, the plurality of elastic rings 16 retract further to seal any fluids within the interior volume of the compact male condom 11 therein.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A compact male condom, comprising:
   a flexible cylindrical body having a closed first end opposite an open second end defining an interior volume;
   wherein the open second end is wrapped about an applicator ring;
   wherein the interior volume is dimensioned to receive a glans of a penis therein;
   a plurality of elastic rings affixed about a circumference of the cylindrical body;
   wherein the plurality of elastic rings is selectively movable between an expanded position and a retracted position;
   wherein a diameter of the cylindrical body is greater when the plurality of elastic rings are in the expanded position than in the retracted position;
   wherein the plurality of elastic rings is biased towards the retracted position;
   wherein the plurality of elastic rings is configured to close the second end when in a retracted position;
   wherein the applicator ring is configured to retain the plurality of elastic rings in the expanded position.

2. The compact male condom of claim 1, wherein the plurality of elastic rings is disposed at regular intervals along a length of the cylindrical body.

3. The compact male condom of claim 2, wherein the plurality of elastic rings is spaced in three-millimeter increments.

4. The compact male condom of claim 1, wherein a diameter of the cylindrical body decreases from the closed first end to the open second end, such that the cylindrical body is configured to contour to the glans.

5. The compact male condom of claim 1, wherein each elastic ring of the plurality of elastic rings comprise circular planar members, such that an interior surface of each of the plurality of rings rests flush against a shaft of the penis.

6. The compact male condom of claim 1, wherein the applicator ring is rigid.

7. The compact male condom of claim 1, wherein the applicator ring is elastic.

8. The compact male condom of claim 1, wherein the applicator ring comprises a toroidal shape.

9. The compact male condom of claim 1, wherein the plurality of elastic rings in the retracted position form a watertight seal.

10. A compact male condom, comprising:
    a flexible cylindrical body having a closed first end opposite an open second end defining an interior volume;
    wherein the interior volume is dimensioned to receive a glans of a penis therein;
    a plurality of elastic rings affixed about a circumference of the cylindrical body;
    wherein the plurality of elastic rings is selectively movable between an expanded position and a retracted position;
    wherein a diameter of the cylindrical body is greater when the plurality of elastic rings are in the expanded position than in the retracted position;
    wherein the plurality of elastic rings is biased towards the retracted position;
    wherein the plurality of elastic rings is configured to close the second end when in a retracted position.

11. The compact male condom of claim 10, wherein the plurality of elastic rings is disposed at regular intervals along a length of the cylindrical body.

12. The compact male condom of claim 11, wherein the plurality of elastic rings is spaced in three-millimeter increments.

13. The compact male condom of claim 10, wherein a diameter of the cylindrical body decreases from the closed first end to the open second end, such that the cylindrical body is configured to contour to the glans.

14. The compact male condom of claim 10, wherein each elastic ring of the plurality of elastic rings comprise circular planar members, such that an interior surface of each of the plurality of rings rests flush against a shaft of the penis.

15. The compact male condom of claim 10, wherein the plurality of elastic rings in the retracted position form a watertight seal.

16. A method for applying a compact male condom, comprising:
    providing a flexible cylindrical body having a closed first end opposite an open second end defining an interior volume, wherein the open second end is wrapped about an applicator ring;
    inserting a glans of a penis through the open second end and into the interior volume;
    sliding the applicator ring along the penis to unwrap the cylindrical body over the glans and the penis such that a plurality of elastic rings affixed about a circumference of the cylindrical body at the second end thereof retract about a shaft of the penis adjacent to the glans;
    removing the applicator ring from the penis such that the cylindrical body is retained thereon;
    whereupon removal of the flexible cylindrical body from the penis, the plurality of elastic rings contract to close the second end entrapping fluids contained within an interior volume of the flexible cylindrical body.

* * * * *